(12) United States Patent
Taylor

(10) Patent No.: US 6,676,632 B2
(45) Date of Patent: *Jan. 13, 2004

(54) IN-LINE IV DRUG DELIVERY PACK WITH CONTROLLABLE DILUTION

(75) Inventor: Michael A. Taylor, Napa, CA (US)

(73) Assignee: PrisMedical Corporation, Napa, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/358,443

(22) Filed: Feb. 3, 2003

(65) Prior Publication Data

US 2003/0114790 A1 Jun. 19, 2003

Related U.S. Application Data

(63) Continuation of application No. 10/214,558, filed on Aug. 6, 2002, now Pat. No. 6,520,932, which is a continuation of application No. 09/717,796, filed on Nov. 20, 2000, now Pat. No. 6,428,505.
(60) Provisional application No. 60/166,597, filed on Nov. 19, 1999.

(51) Int. Cl.[7] .................................. A61M 5/14
(52) U.S. Cl. .............. 604/80; 604/83; 604/85
(58) Field of Search .............. 604/80, 82, 83, 604/85, 84, 246

(56) References Cited

U.S. PATENT DOCUMENTS

| | | |
|---|---|---|
| 3,276,458 A | 10/1966 | Iversen et al. |
| 3,517,816 A | 6/1970 | Huppen |
| 3,730,349 A | 5/1973 | Herrmann |
| 4,070,289 A | 1/1978 | Akcasu |
| 4,160,727 A | 7/1979 | Harris, Jr. |
| 4,231,872 A | 11/1980 | Keil |
| 4,280,912 A | 7/1981 | Berry, III et al. |
| 4,396,383 A | 8/1983 | Hart |
| 4,458,733 A | 7/1984 | Lyons |
| 4,484,920 A | 11/1984 | Kaufman |
| 4,507,114 A | 3/1985 | Bohman et al. |
| 4,511,351 A | 4/1985 | Theeuwes |
| 4,533,348 A | 8/1985 | Wolfe et al. |
| 4,534,757 A | 8/1985 | Geller |
| 4,576,603 A | 3/1986 | Moss |
| 4,648,978 A | 3/1987 | Makinen et al. |
| 4,695,272 A | 9/1987 | Berglund |
| 4,698,153 A | 10/1987 | Matsuzaki et al. |
| 4,784,763 A | 11/1988 | Hambleton et al. |
| 4,810,388 A | 3/1989 | Trasen |
| 4,871,463 A | 10/1989 | Taylor et al. |
| 4,874,366 A | 10/1989 | Zdeb et al. |
| 4,903,717 A | 2/1990 | Sumnitsch |
| 4,994,056 A | 2/1991 | Ikeda |
| 5,004,535 A | 4/1991 | Bosko et al. |
| 5,032,265 A | 7/1991 | Jha et al. |
| 5,059,317 A | 10/1991 | Marius et al. |
| 5,163,922 A | 11/1992 | McElveen, Jr. et al. |
| 5,201,705 A | 4/1993 | Berglund et al. |

(List continued on next page.)

FOREIGN PATENT DOCUMENTS

WO    WO 00 66214 A    11/2000

*Primary Examiner*—Edward K. Look
*Assistant Examiner*—John K Fristoe, Jr.
(74) *Attorney, Agent, or Firm*—Knobbe, Martens, Olson & Bear LLP

(57) ABSTRACT

An in-line drug delivery pack that connects in-line with an intravenous (IV) line and allows for the mixing of diluent with a drug reagent to be delivered to the patient. An internal drug bed bypass mechanism is tailored to apportion diluent flow between the bypass and the drug bed. The apportionment is selected to achieve a solution concentration suitable for IV administration as the dried reagent is dissolved. Thus, both dissolution and precisely tailored dilution are performed in the same simple device.

20 Claims, 4 Drawing Sheets

U.S. PATENT DOCUMENTS

| | | |
|---|---|---|
| 5,259,954 A | 11/1993 | Taylor |
| 5,395,323 A | 3/1995 | Berglund |
| 5,429,603 A | 7/1995 | Morris |
| 5,514,090 A | 5/1996 | Kriesel et al. |
| 5,531,683 A | 7/1996 | Kriesel et al. |
| 5,637,087 A | 6/1997 | O'Neil et al. |
| 5,685,846 A | 11/1997 | Michaels, Jr. |
| 5,725,777 A | 3/1998 | Taylor |
| 6,428,505 B1 | 8/2002 | Taylor |
| 6,520,932 B2 | 2/2003 | Taylor |

IN-LINE IV DRUG DELIVERY PACK WITH CONTROLLABLE DILUTION

REFERENCE TO RELATED APPLICATION

This application is a continuation of U.S. patent application Ser. No. 10/214,558, filed Aug. 6, 2002 now U.S. Pat. No. 6,520,932, which is a continuation of U.S. patent application Ser. No. 09/717,796, filed Nov. 20, 2000 now U.S. Pat. No. 6,428,505, which claims the benefit of priority to U.S. provisional application No. 60/166,597, filed Nov. 19, 1999, all of which are hereby incorporated by reference in their entirety.

BACKGROUND OF THE INVENTION

1. Field of the Invention

The present invention relates generally to drug delivery devices, and more particularly to devices for storing, transporting and dissolving dry reagents.

2. Description of the Related Art

Medical treatments often involve solutions or suspensions of drugs or other reagents to be injected into the human body. Mixing and injecting such solutions can be extremely expensive and inaccurate. Thus, there are a number of problems with current methods of intravenous drug delivery.

Conventional methods involve administration of drug solutions derived from thawed preparations of previously frozen drug solutions or from drug solutions produced by connection of a diluent pouch with a drug-containing vial. The later delivery method requires considerable manipulation to place the dry drug formulation into solution prior to administration to the patient. Among the greatest problems associated with existing methods are the direct and indirect costs of the delivery systems. For frozen solutions indirect costs are associated with freezers, temperature monitoring equipment and procedures required to maintain drug supplies. Direct costs are associated with the labor required to thaw the frozen solutions prior to administration to the patient. Similarly, for preparation of drug solutions using dry drug and separate diluent preparations, costs are associated with the requirement for multiple components and the manipulation required to place the drug in solution.

The requirement for freezing drug solutions or use of multiple components to prepare drug solutions results from the instability of many drugs once the drugs are activated or placed into solution. Over time, sometimes within a matter of 1 to 2 hours, the efficacy of drugs diminishes after they are placed in solution. Accordingly, additional costs are associated with the waste associated with formation of drug solutions that are not administered to the patient in a timely manner, for example, when changes in prescription or patient movement preclude administration of the prepared drug solution.

The manipulation associated with combining a separate drug vial and a diluent from a pouch includes threading of a separate drug-containing vial into a threaded receptacle. Inadequate threading together of these components results in leakage of the diluent or drug solution from this junction and breaches the sterile barrier intended to be formed between the drug vial and the diluent pouch. The repeated effort required to thread these separate components together has lead to carpal tunnel syndrome among healthcare providers. For certain delivery systems, an internal cork must be removed by manipulation through the walls for the diluent pouch in order to expose the dry drug within the vial to the diluent. Omission of this step results in administration of diluent without drug to the patient.

Moreover, in order to properly dissolve the drug in the diluent the combination of components must be vigorously agitated. It is often not possible to be absolutely certain that all the drug has been removed from the vial. Because of the translucent nature of the diluent pouch, it is also sometimes difficult to differentiate between dissolved drug and minute, undissolved drug particles within the diluent pouch. If undissolved drug particles are administered to patients they present a serious potential hazard to the patient of an embolus capable of occluding small blood vessels.

Administration of the additional fluids required for administration of drug solutions using a secondary set of fluids, beyond those administered to maintain electrolyte balance, results in fluid problems in patients with fluid retention maladies.

The volume occupied by existing delivery systems and/or the requirement for maintaining a frozen environment prevents these systems from being used in automated dispensing devices.

An alternative to use of these delivery systems is the preparation of drug solutions by pharmaceutical personnel from bulk containers of drug. These procedures require a considerable amount of effort by these personnel and represents a serious hazard to the pharmacy and drug administration personnel due to the toxicity of some agents.

U.S. Pat. No. 5,259,954 to Taylor, issued Nov. 9, 1993 (hereinafter "the '954 patent") and U.S. Pat. No. 5,725,777 issued Mar. 10, 1998 (hereinafter "the '777 patent") disclose a drug pack or "reagent module" suitable for storing dry reagents and for preparing solutions for administration by passing fluid through the pack. These references are incorporated herein by reference. The '777 patent discloses two embodiments in which a porous compression element constantly exerts an inward force on a dry reagent bed, keeping it compacted even as the bed is eroded by passing fluid through the porous compression element and through the bed. This arrangement advantageously enables efficient uniform dissolution of the reagent bed by avoiding channel formation through the reagent bed.

While the reagent modules of the '954 and '777 patents operate well in storing and dissolving reagent beds efficiently, there remains room for improvement.

SUMMARY OF THE INVENTION

An in-line drug delivery pack that connects in-line with an intravenous (IV) line and allows for the mixing of diluent with a drug reagent to be delivered to the patient. An internal drug bed bypass mechanism is tailored to apportion diluent flow between the bypass and the drug bed. The apportionment is selected to achieve a solution concentration suitable for IV administration as the dried reagent is dissolved.

Thus, both dissolution and precisely tailored dilution are performed in the same simple device.

DETAILED DESCRIPTION OF THE PREFERRED EMBODIMENT

Description of Components

Figure 1:
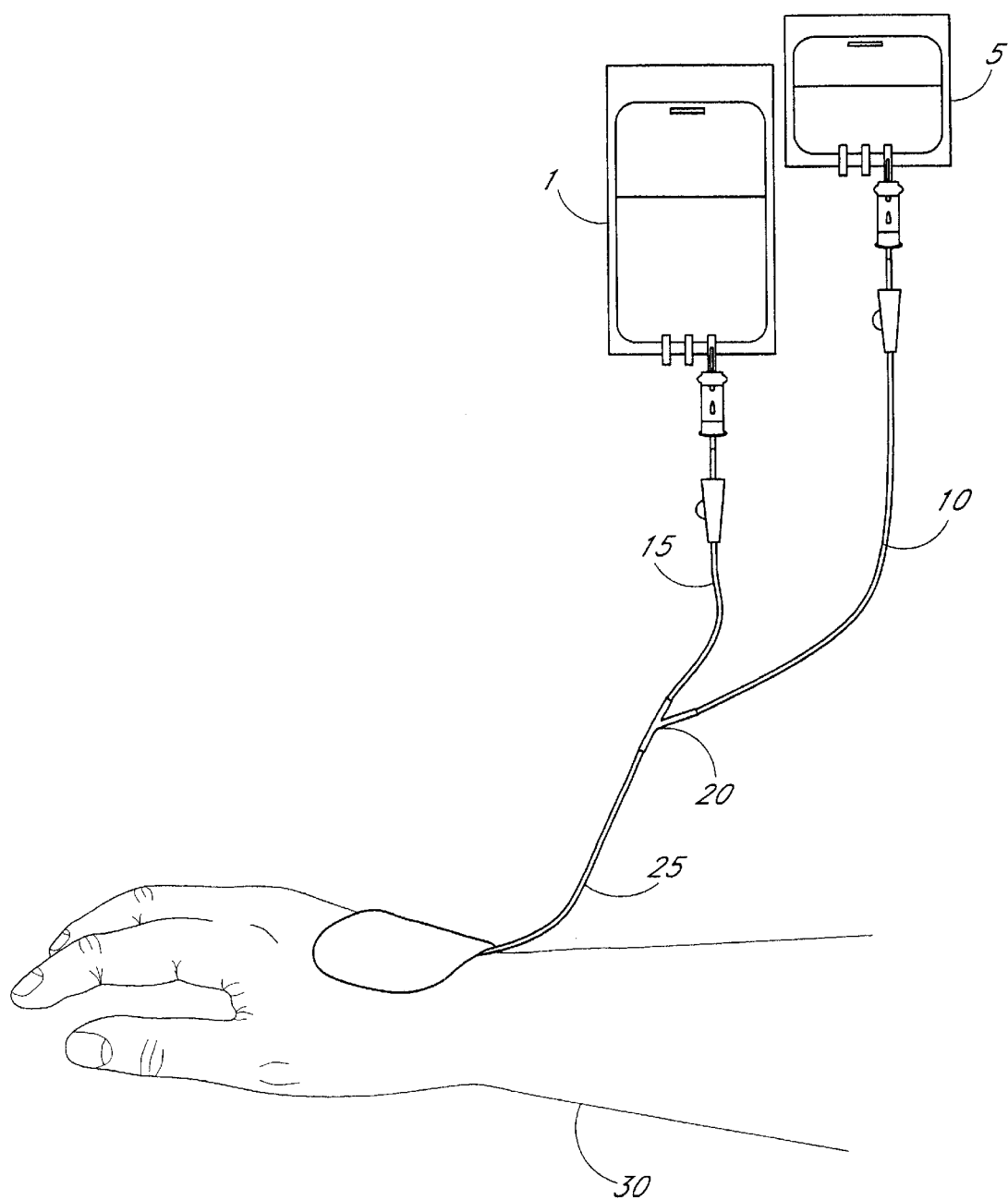
FIG. 1 is an elevational view of an IV line drug delivery system, with a joint connecting a diluent line and a concentrated solution drip.

One drug delivery system is shown in FIG. 1. The intravenous bag 1 is connected to a drug delivery bag 5 by means of a Y-connector 20. The Y-connector 20 combines the solutions into an injection line 25 that is subsequently introduced to the hand 30 or any other body part. The drug delivery bag 5 holds pre-formed concentrated solution, which is diluted for IV injection by fluid from the diluent bag 1. As noted in the Background section, this arrangement has certain disadvantages.

Figure 2:
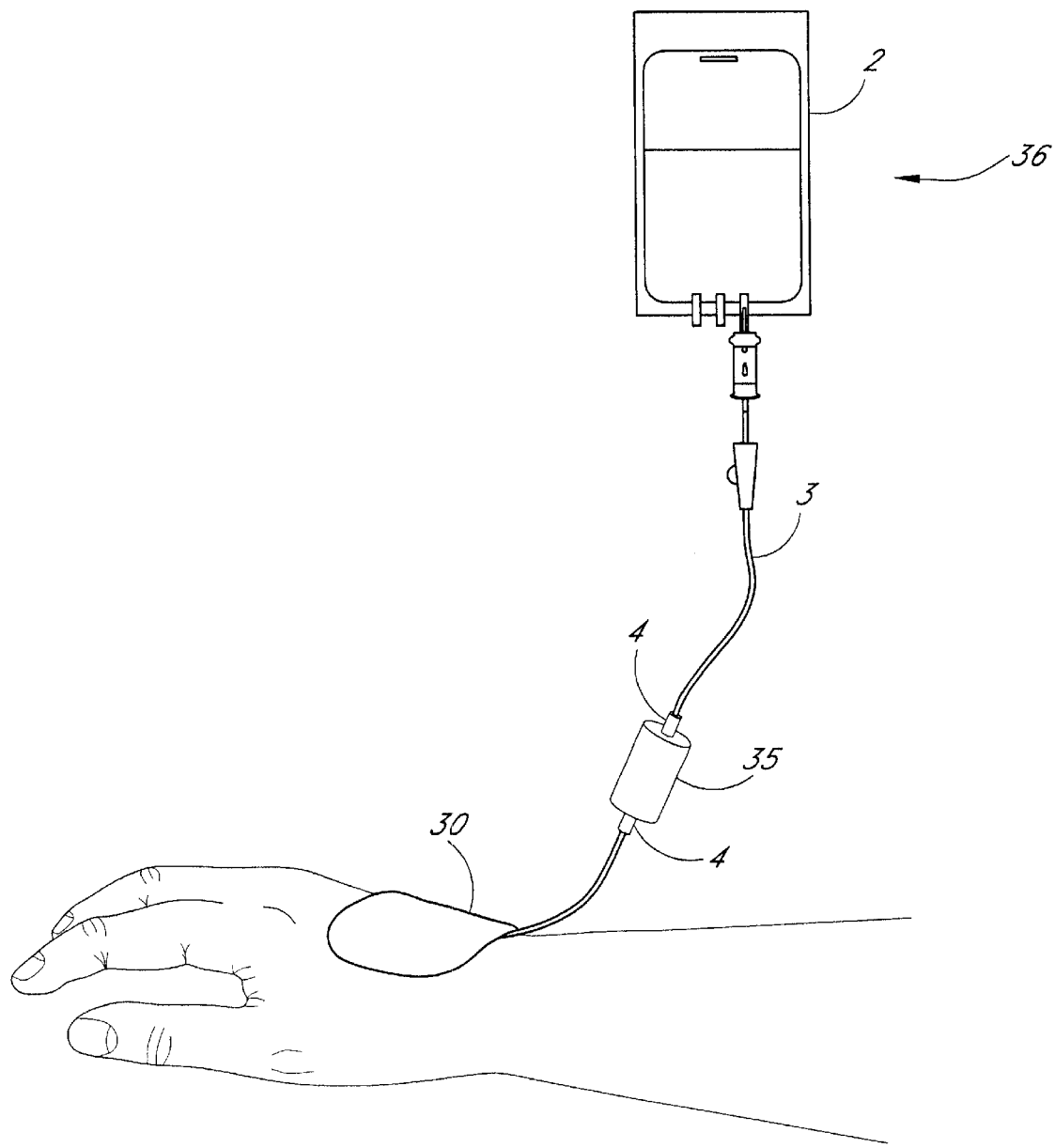
FIG. 2 is an elevational view of an in-line IV drug delivery system, constructed in accordance with a preferred embodiment of the present invention.

With reference to FIG. 2, a drug delivery pack 35 is shown in-line with an intravenous solution bag 1. The solution bag 1 is part of the intravenous delivery system 36. The IV line 3 leads from the intravenous delivery system 36 to the drug delivery pack 35 via Luer locks 4, and then to an injection site 30, which in this example is at a human hand. Those skilled in the art will realize that other injection sites include but are not limited to the arm, neck and leg.

Figure 3:
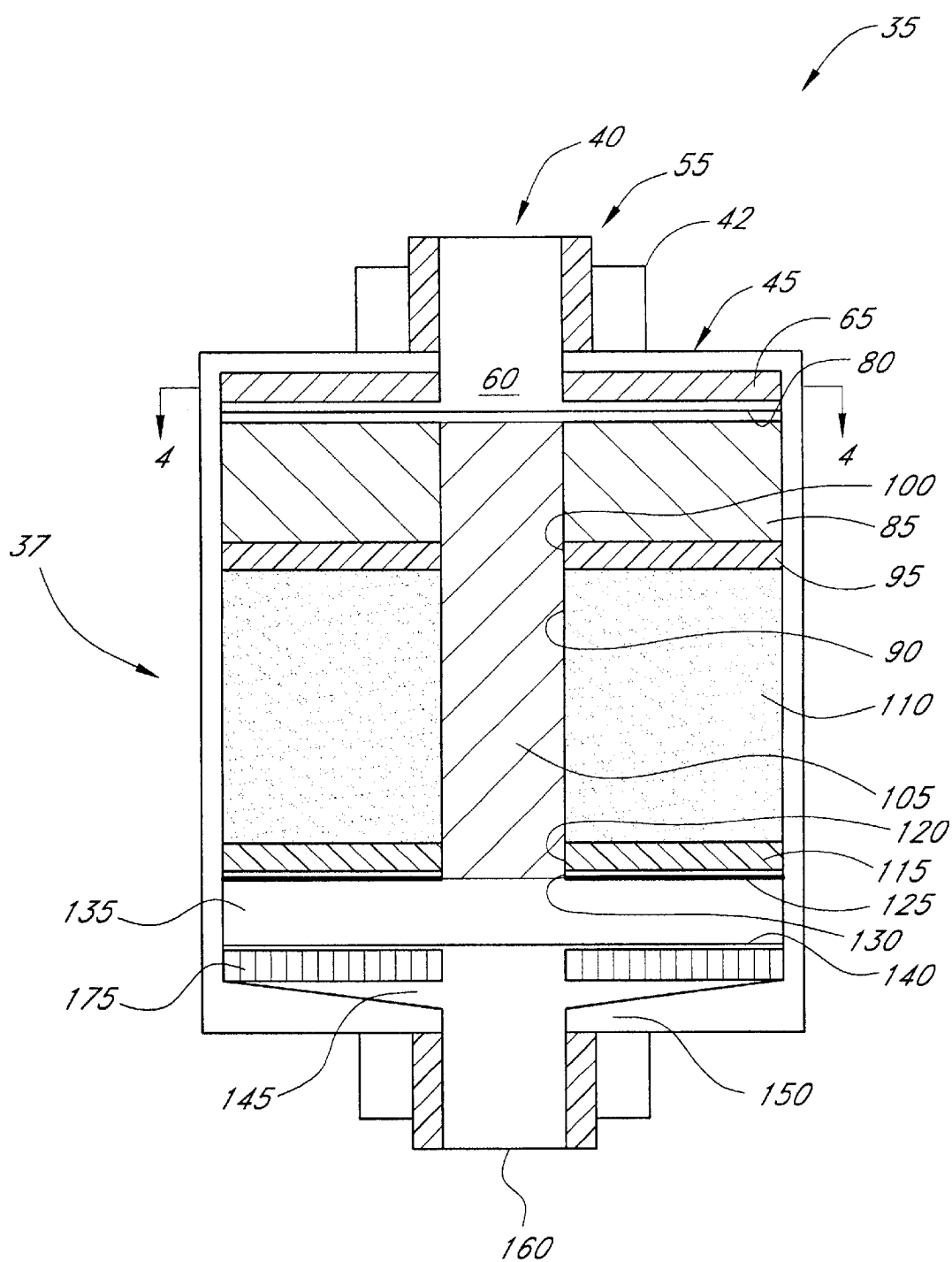
FIG. 3 is an elevational cross-section of a drug delivery pack for use in-line along an IV line.

Now referring to FIG. 3, a housing 37 of the drug delivery pack 35 is preferably composed of a clear material, such as plastic polymer or glass. An inlet 40 in the housing top 45 provides a connection between an input line (not shown), such as an IV line, and the body of the housing 37. The inlet 40 includes a collar 42 terminating at one end with a connection fitting 55 to connect to the diluent source. The housing 37 also contains an air vent (not shown) and a terminal outlet 160 at the axial terminus of the housing 37 opposite to the inlet 40. The air vent is preferably sealed against fluid flow by an air permeable/fluid impermeable barrier or a mechanical valve.

Figure 4:
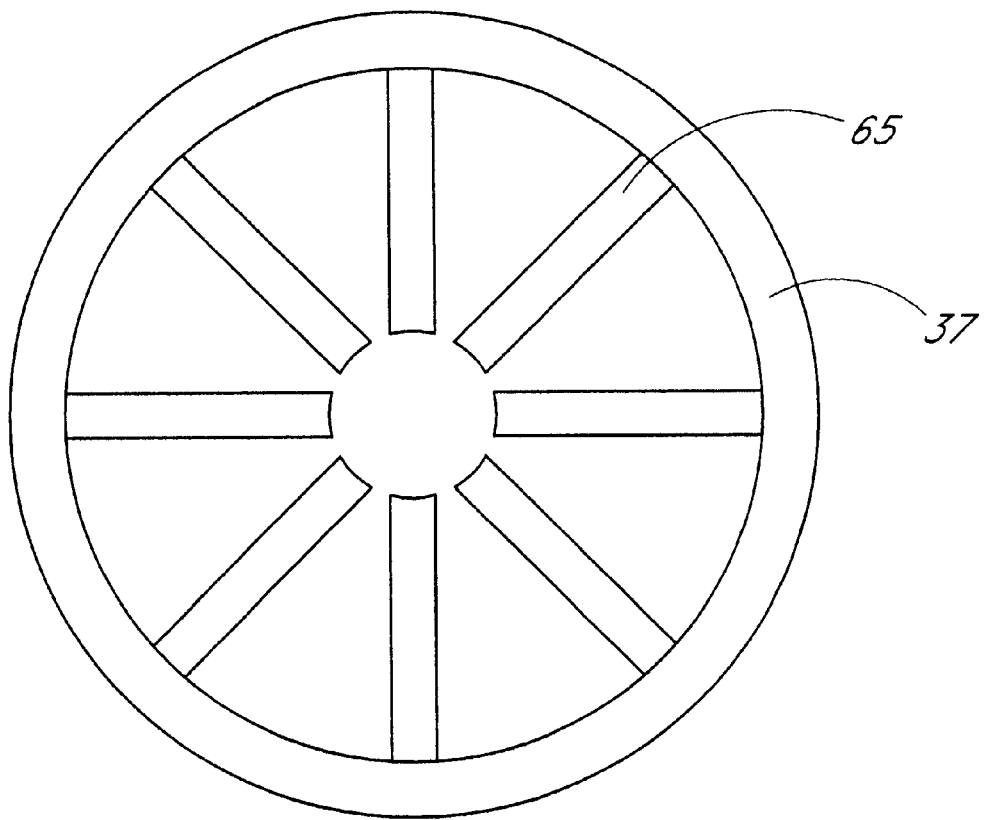
FIG. 4 is a sectional view taken along lines 4—4 in FIG. 3.

Immediately adjacent to the inlet 40 is a distribution chamber 60, defined between an inlet frit 80 and the housing top 45, which are separated by radial fins 65 protruding from the housing top 45. Referring to FIG. 4, the radial fins 65 are shown in a cross-section, stopping short of a central opening.

Referring again to FIG. 3, the inlet frit 80 is a porous material, which can be hydrophilic but is preferably hydrophobic. The porosity of the frit 80 can range from about 5 to about 100 microns, with the preferred range in porosity between about 5 and about 50 microns, and more preferably between about 10 and about 20 microns. Exemplary materials are porous polymers and cellulose filters.

An open bore 90 is located below the inlet frit 80, which is just below the distribution chamber 60. Also below the inlet frit 80 is an upstream compression component 85. The illustrated compression component 85 takes the form of a cylinder surrounding the open central bore 90. The compression component 85 is composed of open celled polymeric material, which upon compression exerts a pressure as a result of memory of the material. This pressure is measured as a compression deflection (CD) or an indentation load deflection (ILD). In other arrangements, the compression component can comprise a polymer or metal spring. The bore 90 is filled with a core 105 of porous material. The core 105 can be tailored as needed, but preferably has a greater porosity in pores per inch (PPI) than the compression component 85.

Below the compression component 85 is an upper reagent restraint 95. In the illustrated embodiment, the upper reagent restraint 95 is a disk of material with a central hole 100 accommodating the core 105. The upper reagent restraint 95 can be porous or nonporous polymeric or cellulosic material. The upper reagent restraint is preferably hydrophilic.

Below the upper reagent restraint 95 is a reagent bed 110. It consists of a fluid soluble material suitable for administering to a patient via dissolution and IV drip. The core 105 also extends through the reagent bed.

Below the reagent bed 110 is a lower reagent restraint 115. The lower reagent restraint 115 comprises a pliable or rigid disk. The restraint can be similar to the upper restraint 95, and is illustrated with a lower reagent central hole 120. If pliable, the lower reagent restraint 115 is preferably backed by a rigid disk 125, as shown. The lower reagent restraint 115 is preferably hydrophobic.

The bore 90 thus extends through the compression component 85, the upper reagent restraint 95, the reagent bed 110, the lower reagent restraint 115 and (if present) the rigid backing 125.

Below the lower reagent restraint 115 and the rigid backing 125, is a collection area 135. The collection area 135 is defined by the housing body 37, the lower reagent restraint 115 or the rigid backing 125.

Below the collection area 135 is a terminal frit 140. The terminal frit 140 consists of porous polymeric material that may have either a hydrophobic or hydrophilic nature. Preferably, the terminal frit 140 is hydrophobic, such that it generates sufficient back-pressure to accumulate fluid in the overlying collection area 135 before passing the fluid.

A collection chamber 145 is located below the terminal frit 140. The collection chamber 145 is defined by the terminal frit 140, the bottom of the housing 150, and the bottom radial fins 175 located adjacent to the housing outlet 160. The outlet end of the pack 35 is thus similar to the inlet end.

The housing outlet 160 forms a tube connecting the housing collection chamber 145 to the exterior of the housing 37. The exterior terminus of the outlet 160 includes a fitting to enable a sterile, closed connection to the downstream portion of the diluent flow. Both the inlet 40 and outlet 160 can be covered by port covers (not shown), if desired, to maintain sterility prior to use.

In operation, with reference to FIG. 2, the drug delivery pack 35 is attached in-line to an intravenous administration set 36 including an upstream reservoir 1 of intravenous fluid connected to a tube 3 linking the reservoir to the patient. Attachment of the drug delivery pack 35 is accomplished by in-line Luer connectors 4 at the inlet and outlet of the drug delivery pack 35. More specifically, on a preexisting IV line, flow is stopped by closing clips (not shown). The intra-line connections are opened and the drug delivery pack 35 is inserted and locked with Luer locks. Next, the closing clips on the fluid line are opened and diluent flow is reestablished. It will be readily apparent to those skilled in the art that a variety of other techniques may be used to connect the drug delivery pack 35 in-line along an IV line. Such techniques include but are not limited to having an IV bag spike at the inlet of the drug delivery pack 35 and/or an IV spike receptacle at the outlet associated with a drip chamber.

Referring now to FIG. 3, diluent from the upstream reservoir 1 (FIG. 2) enters the housing 37 via the inlet 40 and first encounters the inlet radial fins 65. The inlet radial fins 65 cooperate with back-pressure from the inlet frit 80 promote a uniform distribution of diluent across the entire cross-section of the drug delivery pack 35. The downstream fins 65 similarly cooperate with the outlet frit 140 to form a downstream manifold distribution chambers for the solution. The hydrophobic nature of the inlet frit 80 forces the diluent to the periphery within the distribution chamber 60 prior to penetration of the frit 80. Thus, an initially uniform pattern of diluent flow through the upstream portions of the drug delivery pack 35 is established. It will be readily apparent to one skilled in the art that other arrangements can also achieve uniform distribution. Furthermore, the drug pack 35 would also entail advantages without an initial uniform distribution.

The uniform face of diluent enters and passes through the upper compression component 85. After passing through the upper compression component 85, the diluent encounters the preferred upper reagent restraint 95 upstream from the reagent bed 110. The hydrophilic nature of the preferred upper reagent restraint 95 thoroughly "wets" the restraint uniformly by capillary action. This serves to provide a wetting of the entire reagent bed 110. This is particularly advantageous for dissolution of hydrophobic reagents.

A portion of the diluent bypasses the reagent bed 110 by traveling down the porous central core 105 within the bore 90. This diluent accumulates in the collection area 135 above the hydrophobic terminal frit 140. The diameter of the bore 90 holding the core 105, together with the relative porosity and hydrophobocity of the compression component 85, restraint 95, reagent bed 110, and restraint 115, determines the portion of diluent entering the reagent bed 110, as compared to that bypassing the bed 110. Partitioning the amount of diluent that enters the reagent bed 110 effectively regulates the rate of dissolution of that reagent.

Desirably, the hydrophobic nature of the preferred lower reagent restraint 115 retains diluent with the reagent bed 110, enhancing the wetting of the reagent bed 110. Also, a rigid material may be furnished to provide support for the reagent restraint 115. Such material may include but is not limited to sintered plastics.

The solution prepared from the dissolving reagent passes through the reagent bed 110 and exits into the central core 105 and/or through the lower restraint 115.

In the upper collection area 135, the portion of the diluent which bypassed the reagent bed 110 is mixed with the solution formed from diluent passing through the reagent bed 110. The solution is thus diluted within the area 135. Dissolved reagents have time to diffuse to even out concentration in the preferred embodiment. This is due to the fact that enough solution must gather in the collection area 135 to create, preserve and overcome the hydrophobicity of the preferred terminal frit 140. When sufficient solution enters the collection area 155 to create sufficient head pressure to overcome the hydrophobicity of the terminal frit 140, solution terminal frit 140 and into the lower collection chamber 145 and into the housing outlet 160. An additional hydrophobic barrier of varied porosity may also be placed before the outlet. The collection area 135 can also be created by the use of a spring, rather than the rigid and welded elements 115 or 125, as will be apparent to those skilled in the art.

As will be apparent to the skilled artisan in view of the discussion above, the various elements in the drug pack 35 can be arranged to vary the relative diluent flow through the core component 105, as compared to diluent flow through the reagent bed 110. Varying the relative flows thus varies the concentration of drug solution exiting the pack 35. For example, for a given set of materials, the diameter of the bore 90 and core element 105 therein can be varied as desired. Alternatively, for a given bore 90 size, the relative porosity of the core element 105 as compared to that of the upper reagent restraint 95 can be changed. Varying materials to accomplish different levels of hydrophobicity can also influence the relative flow rates. For a given application, accordingly, the skilled artisan can determine an appropriate set of materials and relative dimensions to achieve a desirable solution concentration. Thus, no separate diluent line needs to be employed, and the overall IV administration system is much simplified.

The skilled artisan will readily appreciate, in view of the disclosure herein, numerous other manners of varying the relative flow of diluents through the reagent bed as compared to a bypassing flow. For example, in contrast to the illustrated central core 90 and core element 105 housed therein, a peripheral gap between the reagent bed 110 and the housing 337 can be created by surrounding the bed with a frit having a smaller diameter than the housing 37, spaced therefrom by periodic spacers or ribs, for example. In yet another arrangement, the central core 105 need not extend through each of the elements 85, 95, 110, 115 and 125. Note that the inlet frit can also be made hydrophilic to bias fluid flow coming through the inlet 40, through the central core 105, rather than encouraging a uniform flow distribution at the inlet end. Such an arrangement would produce a more dilute solution than use of a hydrophobic inlet frit 80.

Preferred Materials

In the preferred embodiment, the inlet frit 80 is polypropylene. The compression component 85 is made of an open cell foam. The central core 105 is also made of an open cell foam. The terminal frit 140 is cellulose. The lower reagent restraint 115 is hydrophobic and made of porous polypropylene, to retain diluent within the reagent bed.

The collection area 135 is maintained by a polymer spring with greater force deflection than the upper compression component 85, thus spacing the upper components above the terminal frit 140.

The terminal frit 140 is hydrophobic to form the collection area 135 within the housing 37 upstream of the housing outlet.

Exemplary Application

An example of a device for delivery of a typical antibiotic (for example a cephalosporin like Cefazolin™) with a drug bed 110 of 1000 mg utilizes a housing 37 0.75 inches in internal diameter and a height of 1.25 inches. The internal volume of this housing 37 is roughly 9 milliliters. For appropriate delivery this drug is administered over a period of 40 minutes, forming a total of 60 milliliters of solution at concentration between 10 and 40 milligrams/milliliter.

The interior of the housing 37 is divided into two chambers. The upper chamber contains the compression component 85, the core and the reagent. For exemplary 1000 mg dose of drug, the dry volume is 3.0 milliliters. The preferred compression component has a height of 0.875 inches. The central cavity 90 within this component 85 has an interior diameter of 0.25 inches to accommodate the core 105.

The preferred component 85 has a preferred porosity of about 60 to 90 pores per inch (PPI), more preferably 75 PPI, and a preferred compression load deflection (CLD) of about 0.4 to 0.6 PSI at 25% compression, more preferably 0.5 PSI at this compression. At 65% compression the CLD is preferably about 0.5 to 0.8 PSI, more preferably 0.65 PSI. These CLD were determined by measurement of deflection 50 square inches of material. It is compressed within the housing to fill the area upstream of the reagent bed.

The exemplary core 105 has a height of 0.675 inches and an outer diameter of 0.225 inches. The prosity of this material is preferably 90 to 110 PPI, more preferably 100.

The reagent bed restraints 95, 115 have a preferred range in pore size of 5 to 25 microns, more preferably about 10 microns. The support for the reagent bed restraints 95, 115 preferably has pores of 20 to 80 microns, more preferably 40 to 60 microns. The diameter of the hole in the reagent restraints and the support is about 0.215 inches to accommodate the core 105.

The lower chamber 135 is open with a frit 140 at the distal end of the housing 37, adjacent to the outlet 160. The frit 140 between the open chamber 135 and the outlet 160 preferably has pores of between 5 and 25 microns, more preferably about 10 microns. The frit 140 is preferably hydrophobic, comprising polypropylene. It has a preferred thickness of between 0.25 and 0.75 inches, more preferably 0.5 inches.

Other variations will be apparent for those skilled in the art. For instance, an increased diameter of the housing 37 could be employed with an increased core 105 diameter for hydrophilic reagents to decrease the efficiency of dissolution of the reagent.

What is claimed is:

1. A drug delivery apparatus comprising:
   a housing having an inlet port, an outlet port, and at least one terminal frit;
   a drug reagent bed within the housing, the drug reagent bed in communication with a first fluid flow path between the inlet port and the outlet, wherein the drug reagent bed comprises reagents for the preparation of a solution suitable for intravenous administration; and
   a second fluid flow path within the housing between the inlet port and the outlet port, wherein the second fluid flow path bypasses the drug reagent bed.

2. The apparatus of claim 1, further comprising at least one compression component positioned to expert pressure on the drug reagent bed.

3. The apparatus of claim 2, wherein the at least one terminal frit is hydrophobic.

4. The apparatus of claim 2, wherein the at least one terminal frit has a porosity from about 5 to 100 microns.

5. The apparatus of claim 2, wherein the at least one terminal frit has a porosity from about 10 to 20 microns.

6. The apparatus of claim 1, wherein the second fluid flow path is in the middle of the housing.

7. The apparatus of claim 1, wherein a plurality of elements housed within the housing are selected to tailor relative flow rates along the first and second paths to control a concentration of solution formed from diluent and the drug reagent bed.

8. A drug delivery apparatus comprising:
   a housing having an inlet port and an outlet port, wherein a plurality of elements housed within the housing are selected to tailor relative flow rates along the first and second paths to control a concentration of solution formed from diluent and the drug reagent bed;
   a drug reagent bed within the housing, the drug reagent bed in communication with a first fluid flow path between the inlet port and the outlet;
   a second fluid flow path within the housing between the inlet port and the outlet port, the second fluid flow path bypassing the drug reagent bed.

9. The apparatus of claim 8, further comprising at least one compression component positioned within the housing to exert pressure on the drug reagent bed.

10. The apparatus of claim 8, further comprising at least one hydrophobic terminal frit.

11. The apparatus of claim 8, wherein the second fluid flow path is in the middle of the housing.

12. The apparatus of claim 8, wherein the second fluid flow path is at the periphery of the housing.

13. The apparatus of claim 8, wherein the drug reagent bed comprises reagents for the preparation of a solution suitable for intravenous administration.

14. A drug delivery apparatus comprising:
   a housing having an inlet port, an outlet port, and at least one terminal frit, and at least one compression component;
   a drug reagent bed within the housing, the drug reagent bed in communication with a first fluid flow path between the inlet port and the outlet, wherein the drug reagent bed comprises reagents for the preparation of a solution suitable for intravenous administration, and the compression component is positioned within the housing to exert pressure on the reagent bed; and
   a second fluid flow path within the housing between the inlet port and the outlet port, wherein the second fluid flow path bypasses the drug reagent bed.

15. The apparatus of claim 14, wherein the at least one terminal frit is an inlet frit.

16. The apparatus of claim 14, wherein the at least one terminal frit is an outlet frit.

17. The apparatus of claim 14, wherein the at least one terminal frit is hydrophobic.

18. The apparatus of claim 15, wherein the at least one compression component is positioned upstream of the reagent bed.

19. The apparatus of claim 18, wherein the compression component comprises a celled polymeric material.

20. The apparatus of claim 14, wherein a plurality of elements housed within the housing are selected to tailor relative flow rates along the first and second paths to control a concentration of solution formed from diluent and the drug reagent bed.

* * * * *